(12) United States Patent
Graumann et al.

(10) Patent No.: US 7,634,056 B2
(45) Date of Patent: Dec. 15, 2009

(54) X-RAY SYSTEM AND METHOD FOR COMPOSITION OF X-RAY IMAGES

(75) Inventors: Rainer Graumann, Höchstadt (DE); Sorin-Alexandru Neagu, Erlangen (DE); Sven Martin Sutter, Herzogenaurach (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 12/178,001

(22) Filed: Jul. 23, 2008

(65) Prior Publication Data
US 2009/0028296 A1 Jan. 29, 2009

(30) Foreign Application Priority Data
Jul. 23, 2007 (DE) .................... 10 2007 034 210

(51) Int. Cl.
*G01N 23/04* (2006.01)
*H05G 1/54* (2006.01)
(52) U.S. Cl. .................... 378/62; 378/63; 378/116
(58) Field of Classification Search .................... 378/62, 378/63, 116, 162–166, 196, 197
See application file for complete search history.

(56) References Cited

U.S. PATENT DOCUMENTS

| 6,447,163 | B1* | 9/2002 | Bani-Hashemi et al. ..... 378/205 |
| 6,473,489 | B2 | 10/2002 | Bani-Hashemi et al. |
| 6,574,296 | B2* | 6/2003 | Stierstorfer .................. 378/15 |
| 7,391,846 | B2* | 6/2008 | Verdonck et al. .............. 378/62 |
| 7,436,927 | B2* | 10/2008 | Hempel ....................... 378/63 |

* cited by examiner

*Primary Examiner*—Irakli Kiknadze
(74) *Attorney, Agent, or Firm*—Schiff Hardin LLP

(57) ABSTRACT

In an imaging acquisition system and method, successive x-ray images and successive optical images are respectively acquired from an examination subject. Positional identifiers associated with the examination subject are detected in the optical images, and acquisition of respective x-ray images is triggered only when the identifiers are detected in the optical images. The number of acquired x-ray images is therefore substantially fewer than the number of acquired optical images, and the x-ray images can be acquired with substantially no overlap, thereby avoiding exposing the examination subject to unnecessary radiation.

14 Claims, 2 Drawing Sheets

X-RAY SYSTEM AND METHOD FOR COMPOSITION OF X-RAY IMAGES

BACKGROUND OF THE INVENTION

1. Field of the Invention

The present invention concerns an x-ray system and a method for composition of an aggregate image consisting of multiple individual images.

2. Description of the Prior Art

X-ray exposures are produced for medical diagnosis so that, for example, tissue, vascular and in particular bone structures of body parts can be considered in detail, section by section, using the x-ray images. If individual exposures are not sufficient for diagnostic, therapeutic or operative measures because they depict only a portion of the anatomy of interest, a number of x-ray exposures of the subject to be considered must be produced with a predetermined resolution. This is the case for x-ray imaging of, for example, the spinal column, a leg or an arm, since x-ray images are limited in their dimensions due to a limited detector size. Long hollow bones, the spinal column or even the imaging of a hip joint (including the femur and the knee joint to determine the leg axes, for example) cannot be imaged by means of a single x-ray exposure. When such multiple x-ray images are acquired, they must then be merged exactly with one another, or set in spatial relation to one another, corresponding to the imaged subject. Such image composition can be done, for example, with the acquisition of multiple overlapping x-ray exposures, which can then be exactly spatially associated with one another by means of correlation methods, for example. In order to successfully implement such known correlation methods, however, suitably large overlapping regions must be present. This is disadvantageous for the examination subject because more x-ray exposures must be obtained to cover the anatomy of interest that would be the case for non-overlapping exposures, and therefore a significant increase of the radiation dose to the subject occurs. Moreover, complicated correlation methods are required since few overlapping image parts of x-ray exposures contain suitable correlatable structures.

SUMMARY OF THE INVENTION

An object of the present invention to provide an x-ray system and an associated method to generate an aggregate image that avoid or minimize the above problems.

This object is achieved by an x-ray system and an associated method in accordance with the invention, wherein an x-ray diagnostic unit and an acquisition unit for acquisition of first and second images are provided, and wherein a sequence of first images is delivered by the acquisition unit during a scanning of a subject with natural landmarks, anatomical structures, or applied markers, and a second image is respectively generated by the diagnostic unit in parallel with at least one first image at selected points of the subject. A transformation chain generated based on the sequence of first images is then applied to the sequence of second images.

The invention has the advantage that the radiation exposure due to x-ray exposures for a subject is reduced to the x-ray exposures unavoidable for medical diagnosis.

The invention also has the advantage that the image composition is fast, precise and reproducible.

In the event that additional optical markers are required due to the sterile covering of a surgery field, the invention has the advantage that optical markers necessary for image composition cause no attenuation of the x-rays.

The invention has the further advantage that a simple correlation calculation can be used with markers of simple design or anatomical structures since very high contrasts result in the optical imaging of the markers.

The invention has the advantage that markers or marker structures simply applied on a covering placed over the subject or applied directly on the subject can be used to determine the transformation vectors.

DESCRIPTION OF THE PREFERRED EMBODIMENTS

Figure 1:
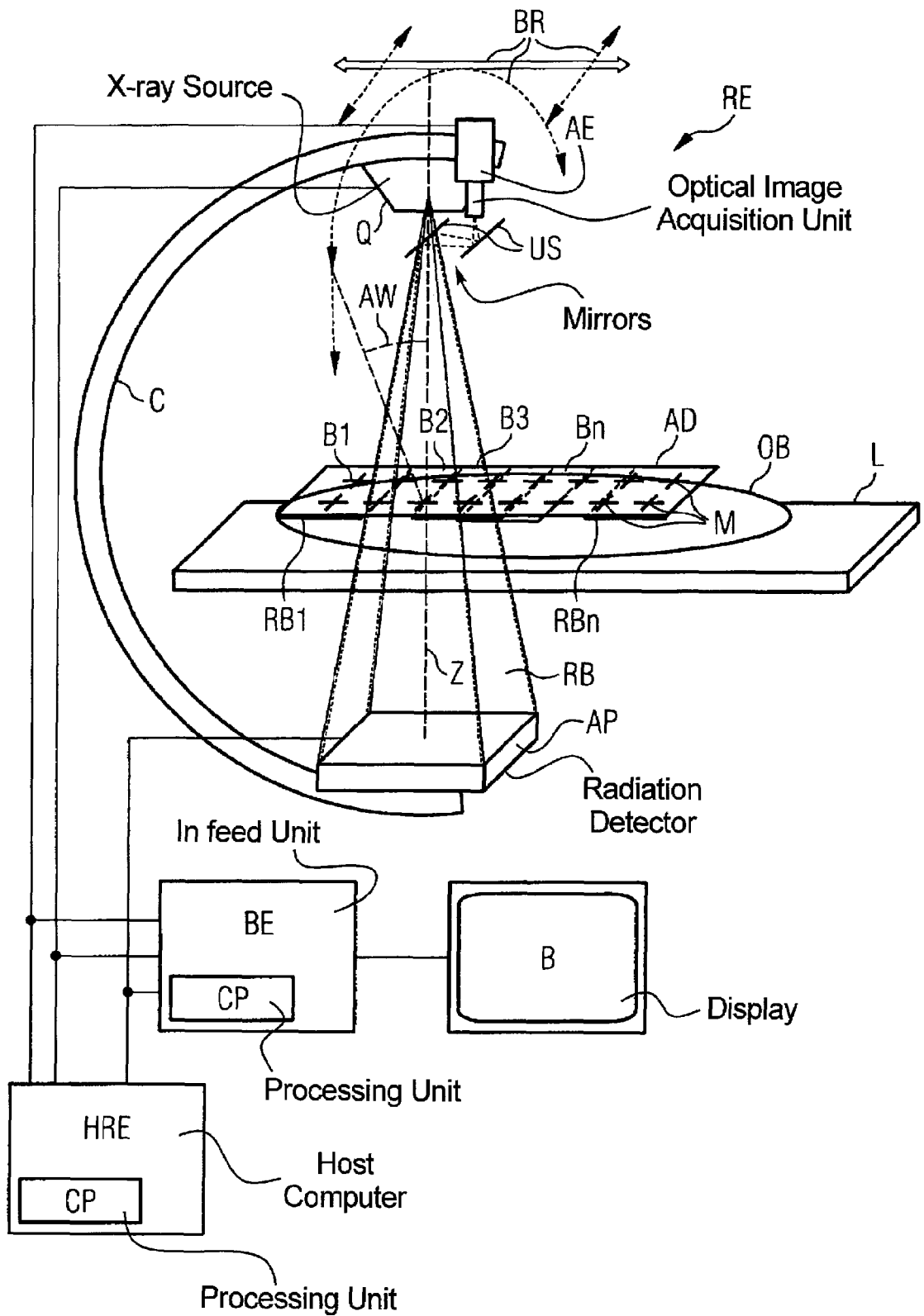
FIG. 1 schematically illustrates an x-ray system constructed and operating in accordance with the present invention.

An x-ray source Q with a detector unit AP corresponding to this is depicted in the shown exemplary embodiment in FIG. 1. The source Q as well as the detector unit AP is respectively arranged at the ends of a C-arm C. The settings required for one or more x-ray exposures RBn can be made in the infeed unit BE belonging to a C-arm system or a host computer HRE.

An acquisition unit AE, such as an optical camera, for acquisition of optical images Bn is arranged such that the acquisition geometry of the x-ray beam exactly coincides with that of the acquisition unit AE. A superimposition of the central ray Z of the x-ray beam RB with the central ray of the optical image can be achieved, for example, by means of deflection mirrors US. A registration of the two image types can be effected once during the installation. The registration must be redone if the arrangement of x-ray source Q/optical image acquisition unit AE changes.

If direct or indirect optical markers are used, the subject OB, or a cloth covering the subject OB, can be provided with simple patterns/markers M in the form of a covering. This covering AD can be a sterile cloth that is placed over the patient OB in a surgical procedure.

Markers M are plotted on the subject OB or the covering AD. The acquisition unit AE can be fashioned as a video camera that scans the surface of a subject OB provided with markers M with a predeterminable acquisition frequency. The x-ray apparatus with the video camera connected therewith can be moved continuously, manually or automatically, over the area of interest of the subject. A number of optical images Bn (first images) are acquired during the continuous optical scanning of the subject. Large overlap regions between two adjacent optical images respectively result due to the high image acquisition frequency (for example 30 images/sec) in connection with a low displacement speed of the C-arm.

The markers or marker structures M applied on the subject OB or the covering AD are detected (controlled by a downstream computer HRE) in an optical image, and associations are established with detected identical structures, markers or marker structures M in a following image. Based on the optical images, a continuous transformation chain is calculated by means of correlation methods.

X-ray images RBn (second images) are acquired only in the regions that are absolutely necessary for a medical diagnosis. The x-ray exposures can be individually, uniquely associated with certain ones (less than all) of the optical images (first images). The triggering of an x-ray image acquired simultaneously and in congruence with a particular optical image Bn can be done with special predetermined anatomical or marker structures detected in the optical images. For example, if a marker M is detected by an image processing program running as well in real time, a resolution unit determines the point in time of the corresponding x-ray image triggering. A possible trigger point in time can be, for example, when the detected marker M is located in the optical image center. For precision, each marker M can exhibit a marker structure, such as a cross, allowing the center of the marker structure to be detected.

Figure 2:
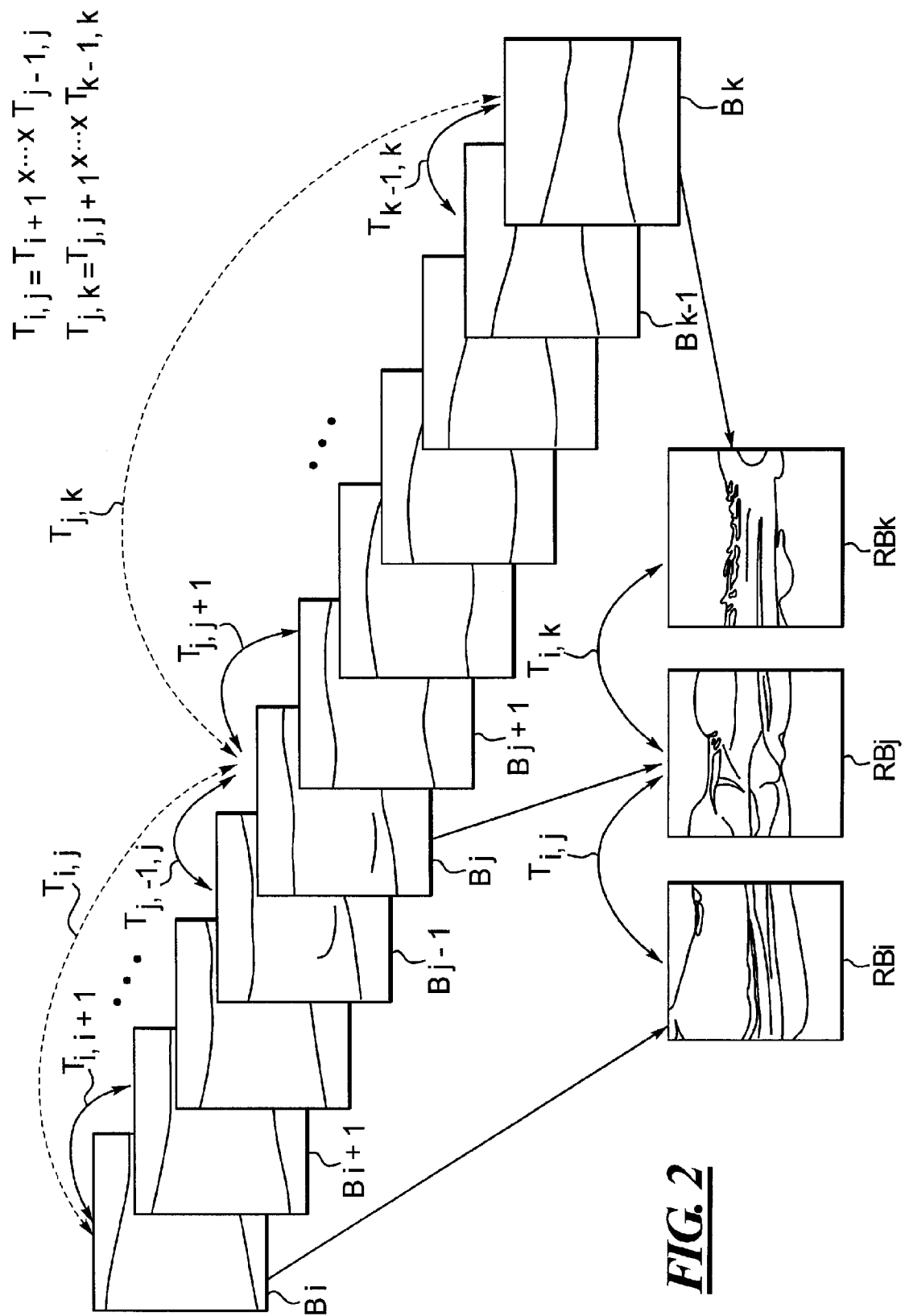
FIG. 2 schematically illustrates a transformation chain for generating an aggregate x-ray image in accordance with the invention.

A processing unit CP arranged in an infeed unit BE or a host computer HRE forms a transformation chain based on detected positions of the same markers M in a sequence of first images Bn. This transformation chain is applied to the second images RBn associated with the respective individual first images Bx, By, . . . . A leg axis beginning at the femoral bone (including knee joint) can be determined thereby. This geometric relationship as shown in FIG. 2 can also be applied to x-ray images RBn acquired in isolation since an optical image is respectively associated with each x-ray image. The transformation chain formed from the multiple optical images can likewise be applied to the x-ray images due to the unique association of certain ones of the x-ray images with the certain ones of the optical images. An aggregate image composed of non-overlapping x-ray images thus can be formed.

The optical images are linked among one another by a transformation chain as shown in FIG. 2. The optical images are depicted in FIG. 2. With regard to the first images Bi, Bi+1, . . . , Bj, Bk−1, Bk, for example, x-ray images RBi, RBj and Rk−1 have been obtained respectively for optical images B1, Bj and Bk−1. A transformation Ti,j and Tj,k are determined by a number of projections or transformations Ti, Ti+1 between the optical images. This transformation equation is applied to the x-ray images as indicated in FIG. 2.

In the case of the use of a cloth-like covering AD with markers or marker structures M, this can also cover the subject to the side of the subject or patient OB. Here an acquisition from arbitrary acquisition angles AW relative to the subject OB is also possible.

The aggregate image and/or any individual optical or x-ray image can be presented at a monitor B.

In this arrangement, the aggregate image generation is also similarly suitable for a 2D or 3D image generation. In the case of 3D imaging, the video image superimposition could occur between the 3D acquisitions; even for 3D imaging, suitable video images can be acquired in parallel.

Due to the capability of implementing an optical zoom of the video camera, the optical region can be significantly enlarged while maintaining the correlation with the x-ray images. This can further simplify the correlation and achieve the possibility to simultaneously superimpose the multiple x-ray images on the larger video image. Overlapping regions are imaged only once for merging the first images.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray image acquisition system comprising:
an x-ray image acquisition system configured to acquire successive x-ray images of an examination subject;
an optical image acquisition system configured to acquire successive optical images of the examination subject; and
a control unit connected to said x-ray image acquisition system and to said optical image acquisition system to control respective acquisition of said successive x-ray images and said successive optical images, said control unit being configured to detect respective identifiers in respective ones of said successive optical images, and to trigger acquisition of said x-ray images only when the respective identifiers are detected in said ones of said optical images, to cause said x-ray image acquisition system to acquire a first plurality of said successive x-ray images that is less than a second plurality of said optical images acquired by said optical image acquisition unit, with substantially no overlap between said successive x-ray images.

2. An image acquisition system as claimed in claim 1 comprising a common carrier on which said x-ray image acquisition system and said optical image acquisition system are both mounted, said carrier simultaneously moving said x-ray image acquisition system and said optical imaging acquisition system along a predetermined movement direction relative to the examination subject.

3. An image acquisition system as claimed in claim 2 wherein said x-ray image acquisition system has an x-ray field of view and wherein said optical imaging system has an optical field of view, and wherein said x-ray imaging system and said optical imaging system are mounted on said carrier with said x-ray field of view and said optical field of view coinciding.

4. An image acquisition system as claimed in claim 1 comprising a covering configured to be draped on the examination subject, said covering having a plurality of optical markers applied thereon forming said respective identifiers.

5. An image acquisition system as claimed in claim 1 comprising a plurality of optical markers applied directly onto the examination subject, forming said respective identifiers.

6. An image acquisition system as claimed in claim 1 comprising a computerized processor configured to calculate a transformation chain from the positions of the respective identifiers in said successive optical images, said transformation chain relating said optical images to each other in position relative to the examination subject.

7. An image acquisition system as claimed in claim 6 wherein said computerized processor is configured to apply said transformation chain to said x-ray images to combine said x-ray images, with substantially no overlap, into an aggregate image of said examination subject.

8. An image acquisition method comprising the steps of:
with an x-ray image acquisition system, acquiring successive x-ray images of an examination subject;
with an optical image acquisition system, acquiring successive optical images of the examination subject; and
automatically controlling respective acquisition of said successive x-ray images and said successive optical images, by detecting respective identifiers in respective ones of said successive optical images, and triggering acquisition of said x-ray images only when the respective identifiers are detected in said ones of said optical images, to cause said x-ray image acquisition system to acquire a first plurality of said successive x-ray images that is less than a second plurality of said optical images acquired by said optical image acquisition unit, with substantially no overlap between said successive x-ray images.

9. An image acquisition method as claimed in claim 8 comprising mounting said x-ray image acquisition system and said optical image acquisition system on a common carrier, and simultaneously moving said x-ray image acquisition system and said optical imaging acquisition system on said carrier along a predetermined movement direction relative to the examination subject.

10. An image acquisition method as claimed in claim 9 wherein said x-ray image acquisition system has an x-ray field of view and wherein said optical imaging system has an optical field of view, and comprising mounting said x-ray imaging system and said optical imaging system on said carrier with said x-ray field of view and said optical field of view coinciding.

11. An image acquisition method as claimed in claim 8 comprising draping the examination subject with a covering, and providing said covering on a plurality of optical markers forming said respective identifiers.

12. An image acquisition method as claimed in claim 8 comprising directly applying a plurality of optical markers onto the examination subject, to form said respective identifiers.

13. An image acquisition method as claimed in claim 8 comprising automatically calculating a transformation chain from the positions of the respective identifiers in said successive optical images, said transformation chain relating said optical images to each other in position relative to the examination subject.

14. An image acquisition method as claimed in claim 13 comprising automatically applying said transformation chain to said x-ray images to combine said x-ray images, with substantially no overlap, into an aggregate image of said examination subject.

* * * * *